United States Patent [19]

Stemmann

[11] Patent Number: 5,611,689
[45] Date of Patent: Mar. 18, 1997

[54] POSITIONING DEVICE FOR CONNECTING A PROSTHESIS TO A BODY IMPLANT

[76] Inventor: Hartmut Stemmann, Kollaustr. 6, 2000 Hamburg 54, Germany

[21] Appl. No.: 406,592

[22] Filed: Mar. 20, 1995

Related U.S. Application Data

[62] Division of Ser. No. 75,290, Jun. 11, 1993, Pat. No. 5,421,722.

[30] Foreign Application Priority Data

Jun. 12, 1992 [DE] Germany ............................ 9207951 U

[51] Int. Cl.⁶ .................................................. A61C 13/22
[52] U.S. Cl. .................................................. 433/189; 24/303
[58] Field of Search ..................................... 433/189, 172, 433/173, 174; 24/303; 335/303, 306

[56] References Cited

U.S. PATENT DOCUMENTS

| | | |
|---|---|---|
| 3,378,893 | 4/1968 | Labek ........................................ 24/303 |
| 3,690,005 | 9/1972 | Edelman . |
| 4,184,252 | 1/1980 | Krol et al. . |
| 4,251,791 | 2/1981 | Yanagisawa et al. . |
| 4,482,034 | 11/1984 | Baermann . |
| 4,508,507 | 4/1985 | Jackson . |
| 4,643,604 | 2/1987 | Enrico ................................... 335/306 X |
| 4,815,975 | 3/1989 | Garrel et al. . |
| 4,991,270 | 2/1991 | Aoki ........................................ 24/303 |
| 4,993,950 | 2/1991 | Mensor, Jr. . |
| 4,997,372 | 3/1991 | Shiner et al. . |
| 5,042,116 | 8/1991 | Ossiani ..................................... 24/303 |
| 5,108,288 | 4/1992 | Perry ....................................... 433/173 |
| 5,123,843 | 6/1992 | Van der Zel et al. . |

FOREIGN PATENT DOCUMENTS

| | | |
|---|---|---|
| 0347510 | 12/1989 | European Pat. Off. . |
| 3739434 | 5/1988 | Germany . |
| 8803488.7 | 7/1988 | Germany . |
| 9306146 | 9/1993 | Germany . |
| 4328779 | 3/1994 | Germany . |

Primary Examiner—Nicholas D. Lucchesi
Attorney, Agent, or Firm—Burns, Doane, Swecker & Mathis, L.L.P.

[57] ABSTRACT

A magnet arrangement is provided having mutually opposing, cylindrical magnets for securing a prosthesis, one magnet being implanted or fastened to an implant and the opposing magnet being fitted in a prosthesis, in particular a dental prosthesis, wherein the bearing surface of the one magnet is of convex configuration and the bearing surface of the opposing magnet is of concave configuration corresponding to the radius of curvature of the convex bearing surface of the other magnet.

15 Claims, 2 Drawing Sheets

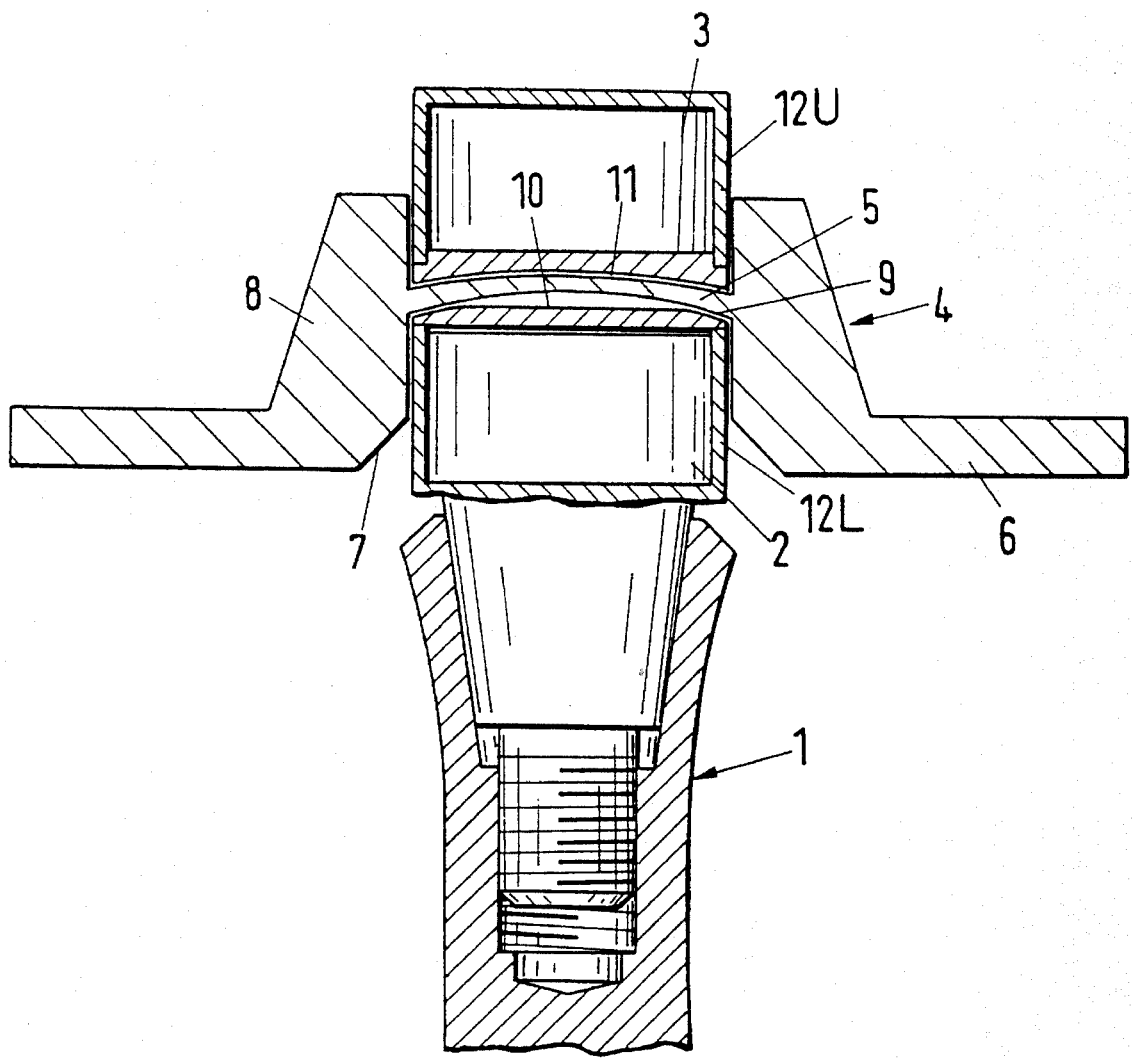

POSITIONING DEVICE FOR CONNECTING A PROSTHESIS TO A BODY IMPLANT

RELATED INVENTION

The present application is a division of U.S. Ser. No. 08/075,290 filed Jun. 11, 1993 now U.S. Pat. No. 5,421,722 by the applicant of record.

BACKGROUND OF THE INVENTION

The invention relates to a magnet arrangement for securing a prosthesis, in particular a dental prosthesis, one magnet to be implanted or fastened to an implant and the opposing magnet to be disposed in a prosthesis.

In order, in a magnet arrangement of this type, to obtain a self-centering action when the magnet fastened in the prosthesis is displaced relative to the implanted magnet, for example in chewing motions, the surface of the one magnet is of convex configuration and that of the opposing magnet is, correspondingly, of concave configuration. When, in chewing motions, the prosthesis becomes somewhat displaced in relation to the implanted magnet, a corresponding displacement of the magnet disposed in the prosthesis takes place, whereupon the latter is automatically returned by the magnetic force into the aligned position once the forces acting upon the prosthesis cease.

Furthermore, by virtue of the present invention, a device for positioning a magnet in a prosthesis is proposed, by means of which a magnet to be fitted in a dental prosthesis can be positioned in exact and accurate alignment with an already implanted magnet.

BRIEF DESCRIPTION OF THE DRAWINGS

By way of example, embodiments of the invention are explained in greater detail below with reference to the drawing, in which:

FIG. 2 shows, in section, the two magnets in conjunction with the positioning device.

DETAILED DESCRIPTION OF A PREFERRED EMBODIMENT OF THE INVENTION

Figure 1:
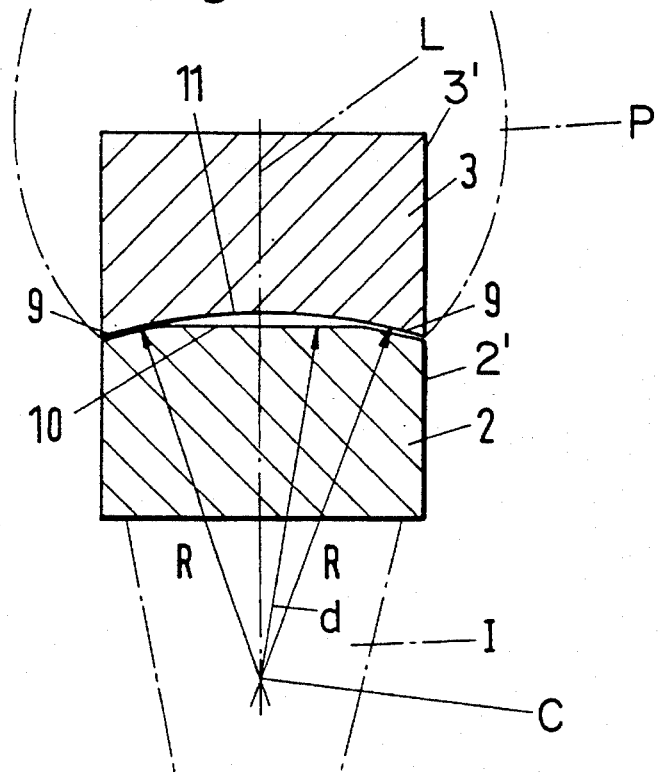
FIG. 1 shows, in a longitudinal section, two mutually adjoining cylindrical magnets.

FIG. 1 shows, in longitudinal section, a cylindrical magnet 2, which is implanted or fastened to an implant I, and an opposing cylindrical magnet 3, which is fastened in a prosthesis P. The magnet 2 includes a cylindrical side wall 2' and a front bearing surface 9, 10 disposed at one end of the side wall 2'. The magnet 3 includes a cylindrical side wall 3' and a bearing surface 11 disposed at one end of the side wall 3'. The front face 10, lying perpendicular to the longitudinal axis of the cylindrical magnet 2, is rounded in the marginal region 9, such that a convex spherical ring surface 9 is produced having a radius R starting from the axis of the cylindrical magnet.

The opposing front face 11 of the magnet 3 is of continuously concave configuration of the same spherical radius R, so that the two mutually adjoining magnets 2 and 3 bear upon each other only in the marginal region 9, whereas, in the central region of the flat front face 10, there is a clearance between the opposing surfaces. That is, in FIG. 1 the distance d is shorter than radius R. The radii R have a common origin C lying on a longitudinal axis L defined by the cylindrical walls 2', 3'. In this way, a pressure point in the centre of the magnet when supporting the prosthesis is avoided and a self-centering action of the magnets 2 and 3, bearing one upon the other, is produced when the magnet 3 disposed in the prosthesis is deflected in relation to the implanted magnet 2 by displacement motions of the prosthesis.

Instead of being provided with a flattened face 10, the bearing surface of the magnet 2 could comprise a continuous convex spherical surface (not shown), but this results, upon a deflection motion of the magnet 3, in the latter being raised more considerably from the magnet 2 when, for example, the magnet 3 is displaced transversely to the axis of the arrangement. As a result of the flattening at 10, the magnet 3 is not so considerably raised when it is moved transversely to the axis.

FIG. 2 shows a magnet arrangement having magnets 2 and 3 respectively welded in casings 12L, 12U, the concave surface 11 and the spherical ring surface 9 being configured on the opposing surfaces of the respective casing 12L, 12U. At 1, the head part of a dental implant is indicated schematically, in which implant there is inserted the cylindrical magnet 2 with the casing 12L. In order to make it easier to position the magnet 3 accurately in a dental prosthesis P, a sleeve-shaped element 4 is provided, this being made from a soft silicone which is licensed in the medical field. The sleeve-shaped element 4 having the sleeve body 8 has, in the lower section, an internal diameter corresponding to the external diameter of the implanted magnet assembly 2, 12L, thereby enabling the sleeve body 8 to be mounted. On the inner periphery, the sleeve body 8 is provided with a partition 5 of predetermined thickness, which partition, on the one hand, limits the depth of immersion of the implanted magnet assembly 2, 12L in the sleeve body 8 and, on the other hand, acts as a spacer for the magnet assembly 3, 12U inserted in the sleeve body 8 from above. The upper section of the sleeve body 8 therefore has an internal diameter corresponding to the external diameter of the magnet assembly 3, 12U. The partition 5 produces a defined air gap between the magnets, which air gap equalises the different resilience of the jaw mucosa when stressed by the dental prosthesis as a result of chewing motions.

The sleeve body 8 has, in the upper region, a wall thickness of approximately 1 mm, which increases in the downward direction to approximately 2 mm, thereby giving rise to a frustoconical outer periphery of the sleeve body 8. Extending radially outwards from the lower edge of the sleeve body 8 is a cover flange 6, which can have, for example, an external diameter of approximately 16 mm. This flange 6 serves to cover the mucosa and can be adapted by the dentist, by cutting to size, according to the respective jaw proportions. For the easier mounting of the element 4 onto the implanted magnet assembly 2, 12L, the lower opening of the sleeve body 8 is bevelled at 7.

Figure 3:
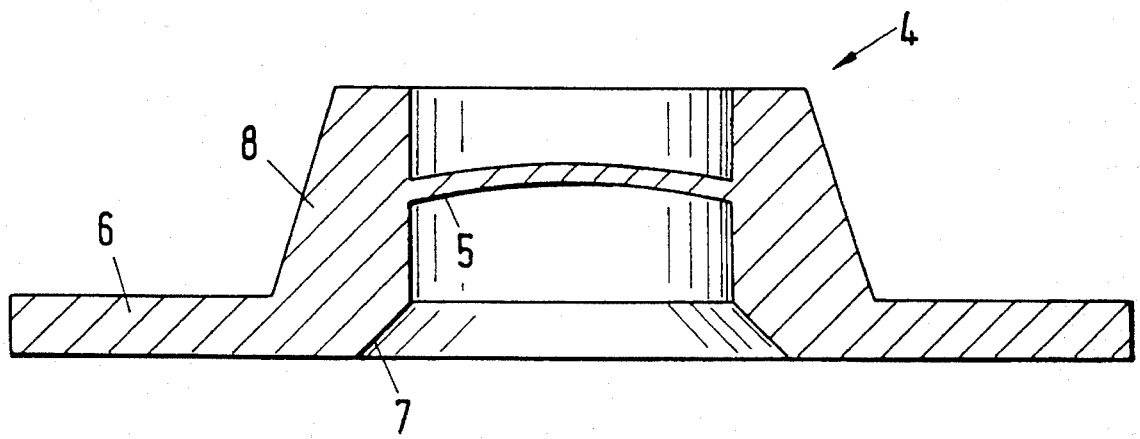
FIG. 3 shows the positioning device in section.

When fitting the magnet holder, the lower magnet assembly 2, 12L is first screwed into the implant 1, whereupon the soft silicone element 4 is mounted onto the magnet 2 assembly, 12L. The flange 6 covers the mucosa and the thicker, lower section of the sleeve body 8 tightly encloses the magnet assembly 2, 12L. The partition 5 bears primarily upon the spherical ring surface 9. For this purpose, the partition 5 is formed onto the sleeve body in a somewhat upwardly arched configuration, as shown by FIG. 3. The upper magnet 3 is then pressed in as far as the stop on the partition 5. The distance between the upper edge of the sleeve body 8 and the partition 5 is designed such that the magnet assembly 3, 12U protrudes from the sleeve body 8 by a pre-specified amount, for example, 1.5 mm. With this exposed retention surface, the upper magnet assembly 3, 12U is inserted into the prefabricated recess of the dental prosthesis (not represented in FIG. 2). The magnet assembly 3, 12U is thereupon incorporated by polymerisation into the prosthesis by means of liquid autopolymerisate. The sleeve body 8 with cover flange 6 and partition 5 prevents the liquid autopolymerisate from wetting the magnet assembly 2, 12L and the implant.

Once the polymerisate has hardened, the element 4 is removed. As a result of the conical shape of the sleeve body 8, a predetermined cavity is formed between the base of the dental prosthesis and the top part of the implant or the magnet assembly 2, 12L, which cavity extends into the oral cavity, so that, in the event of a displacement motion of the prosthesis transversely to the longitudinal axis, the prosthesis base cannot be supported on the magnet assembly 2, 12L. Any damage to the prosthesis is thereby prevented and undesirable, horizontal thrust forces which would have a harmful effect upon the implant are not transmitted from the prosthesis to the implant anchored firmly in the bone.

The full height of the element 4 in the represented illustrative embodiment can amount, for example, to 3.7 mm. The internal diameter measures 4.4 mm. The partition 5 can be designed having a different thickness to enable the air gap between the magnets to be adapted to different resiliences of the oral mucosa. An embodiment is also possible in which the partition 5 is dispensed with, for example in the case of a terminal dental crown. In this case, the two magnets could bear directly upon each other, as shown by FIG. 1, being centred relative to each other by the sleeve body 8.

In place of the partition 5, radially inwardly projecting lugs can also be formed, as spacers, onto the sleeve body 8. Preferably, a closed partition 5 is provided in order to prevent the penetration of liquid polymerisate.

The element 4 can not only be used for centring the magnet arrangement according to FIG. 1, but also for other magnet pairings in which the two magnets lie opposite each other across a flat end face running perpendicular to the longitudinal axis.

I claim:

1. A positioning element for positioning a prosthesis relative to an implant for a human body, the positioning element having a sleeve-shaped portion forming first and second compartments aligned along an axis for receiving respective connector portions of a prosthesis and an implant, said compartments being separated by a partition wall and opening in opposite axial directions, said partition wall being recessed in its entirety with respect to open ends of both of said compartments, said positioning element further including a flange structure extending outwardly from said sleeve-shaped portion in a direction oriented transversely relative to said axis, wherein said positioning element is formed of a soft silicone material.

2. The positioning element according to claim 1, wherein said flange structure extends from an open end of one of said compartments.

3. The positioning according to claim 2, wherein said flange is an annular flange extending annularly about said axis.

4. The positioning according to claim 3, wherein said sleeve-shaped portion, said partition wall, and said annular flange are of one-piece structure.

5. The positioning element article according to claim 1, wherein said flange structure is an annular flange extending annularly about said axis.

6. The positioning element according to claim 1, wherein said sleeve-shaped portion, said partition wall, and said flange structure are of one-piece structure.

7. The positioning element according to claim 1, wherein each of said compartments includes a non-magnetic side wall.

8. The positioning element according to claim 1, wherein each of said compartments includes a non-magnetic side wall.

9. The positioning element according to claim 1 wherein said partition wall is a solid member.

10. A positioning element for positioning a prosthesis relative to an implant for a human body, the positioning element having a sleeve-shaped portion forming first and second compartments aligned along an axis for receiving respective connector portions of a prosthesis and an implant, said compartments being separated by a partition wall and opening in opposite axial directions, said partition wall being recessed in its entirety with respect to open ends of both of said compartments, said positioning element further including a flange structure extending outwardly from said sleeve-shaped portion in a direction oriented transversely relative to said axis, said partition wall including a concave surface facing one of said compartments, and a convex surface facing the other of said compartments.

11. The positioning element according to claim 10, wherein said positioning element is formed of a soft silicone material.

12. A device for connecting a prosthesis to an implant for a human body, the device comprising a positioning element and a pair of magnets, said positioning element having a sleeve-shaped portion forming first and second compartments aligned along an axis and receiving respective ones of said magnets, said compartments being separated by a partition wall and opening in opposite axial directions, said partition wall being recessed in its entirety with respect to open ends of both of said compartments, said positioning element further including a flange structure extending outwardly from said sleeve-shaped portion in a direction oriented transversely relative to said axis.

13. The device according to claim 12, wherein said partition wall includes a concave surface facing one of said compartments, and a convex surface facing the other of said compartments.

14. The device according to claim 12, wherein said positioning element is formed of a soft silicone material.

15. The device according to claim 14, wherein said partition wall includes a concave surface facing one of said compartments, and a convex face facing the other of said compartments.

* * * * *